(12) United States Patent
Powell et al.

(10) Patent No.: US 11,406,664 B2
(45) Date of Patent: Aug. 9, 2022

(54) FERRIC MALTOL COMPOSITIONS FOR USE IN THE TREATMENT OR PREVENTION OF CANCER AND TUMOURS

(71) Applicant: Shield TX (UK) Limited, Gateshead (GB)

(72) Inventors: Jonathan Joseph Powell, Cambridge (GB); Dora I. A. Pereira, Cambridge (GB)

(73) Assignee: SHIELD TX (UK) LIMITED, Gateshead (GB)

( * ) Notice: Subject to any disclaimer, the term of this patent is extended or adjusted under 35 U.S.C. 154(b) by 145 days.

(21) Appl. No.: 16/089,720

(22) PCT Filed: Mar. 31, 2017

(86) PCT No.: PCT/EP2017/057705
§ 371 (c)(1),
(2) Date: Sep. 28, 2018

(87) PCT Pub. No.: WO2017/167972
PCT Pub. Date: Oct. 5, 2017

(65) Prior Publication Data
US 2020/0306293 A1    Oct. 1, 2020

(30) Foreign Application Priority Data

Mar. 31, 2016    (GB) .................................. 1605474

(51) Int. Cl.
| | | |
|---|---|---|
| *A61K 33/26* | (2006.01) | |
| *A61K 31/351* | (2006.01) | |
| *A61K 9/00* | (2006.01) | |
| *A61K 9/28* | (2006.01) | |
| *A61K 9/48* | (2006.01) | |
| *A61K 45/06* | (2006.01) | |

(52) U.S. Cl.
CPC ............ *A61K 33/26* (2013.01); *A61K 31/351* (2013.01); *A61K 9/0019* (2013.01); *A61K 9/0031* (2013.01); *A61K 9/0053* (2013.01); *A61K 9/28* (2013.01); *A61K 9/4891* (2013.01); *A61K 45/06* (2013.01)

(58) Field of Classification Search
CPC ........... A61K 33/26; A61K 45/06; A61K 9/28
See application file for complete search history.

(56) References Cited

FOREIGN PATENT DOCUMENTS

| WO | WO 03/097627 | 11/2003 |
|---|---|---|
| WO | WO 2012/101442 | 8/2012 |

(Continued)

OTHER PUBLICATIONS

Evstatiev, Rayko, et al. "iron (ni)-Sodium-EDTA, as used for food fortification, aggravates intestinal inflammation and drives tumorigenesis in mouse models of colitis-associated cancer." Zeitschrifl fur Gastroenteroloeie 53.05 (2015): p. 03. (Year: 2015).*

(Continued)

*Primary Examiner* — Jared Barsky
*Assistant Examiner* — Janet L Coppins
(74) *Attorney, Agent, or Firm* — Parker Highlander PLLC

(57) ABSTRACT

The use of ferric maltol compositions for the treatment or prevention of cancer and tumours is disclosed, in particular for the treatment or prevention of gastrointestinal cancers or gastrointestinal tumours, such as large bowel (colorectal), small bowel or upper gastrointestinal cancers.

21 Claims, 3 Drawing Sheets

(56) References Cited

FOREIGN PATENT DOCUMENTS

WO  WO 2015/101971     1/2015
WO  WO-2015101971 A1 * 7/2015 ............... A61P 1/00

OTHER PUBLICATIONS

Weitz et al., Lancet 2005, vol. 365, pp. 153-165. (Year: 2005).*
Yasumoto et al., Anticancer Research (2004), vol. 24, pp. 755-762. (Year: 2004).*
Kim et al., Tumor Biol (2016), vol. 37, pp. 9709-9719. (Year: 2016).*
Wilson et al, Int J. Colorectal Dis (2017), vol. 32, 1617-1624. (Year: 2017).*
Evstatiev, Rayko, et al. "Iron (IIT)-Sodium-EDTA, as used for food fortification, aggravates intestinal inflammation and drives tumorigenesis in mouse models of colitis-associated cancer." *Zeitschrift für Gastroenterologie* 53.05 (2015): P03.
Gasche et al. "Ferric maltol is effective in correcting iron deficiency anemia in patients with inflammatory bowel disease: results from a phase-3 clinical trial program." *Inflammatory Bowel Diseases* 21.3 (2014): 579-588.
International Search Report and Written Opinion issued in International Application No. PCT/EP2017/057705, dated Jun. 30, 2017.
Mergler, Bianca I., et al. "Development of the Caco-2 model for assessment of iron absorption and utilisation at supplemental levels." *J Pharm Nutr Sci* 2.1 (2012): 27-34.
Murakami, Keiko, et al. "Maltol/iron-mediated apoptosis in HL60 cells: participation of reactive oxygen species." *Toxicology letters* 161.2 (2006): 102-107.
Pereira, Dora IA, et al. "A rapid, simple questionnaire to assess gastrointestinal symptoms alter oral ferrous sulphate supplementation." *BMC gastroenterology* 14.1 (2014): 1-8.
Radulescu, Sorina, et al. "Luminal iron levels govern intestinal tumorigenesis after Apc loss in vivo." *Cell reports* 2.2 (2012): 270-282.
Search Report issued in United Kingdom Application No. 1605474. 4, dated Jan. 6, 2017.
Seril, Darren N., et al. "Systemic iron supplementation replenishes iron stores without enhancing colon carcinogenesis in murine models of ulcerative colitis: comparison with iron-enriched diet." *Digestive diseases and sciences* 50.4 (2005): 696-707.
Tolkien, Zoe, et al. "Ferrous sulfate supplementation causes significant gastrointestinal side-effects in adults: a systematic review and meta-analysis." *PloS one* 10.2 (2015): e0117383.
Yasumoto et al. "Cytotoxic activity of deferiprone, maltol and related hydroxyketones against human tumor cell lines." *Anticancer Research* 24.2B (2004): 755-762.

* cited by examiner

FERRIC MALTOL COMPOSITIONS FOR USE IN THE TREATMENT OR PREVENTION OF CANCER AND TUMOURS

This application is a national phase application under 35 U.S.C § 371 of International Application No. PCT/EP2017/057705 filed Mar. 31, 2017, which claims priority to United Kingdom Application No. 1605474,4, filed Mar. 31, 2016. The entire text of each of the above referenced disclosures is specifically incorporated herein by reference.

FIELD OF THE INVENTION

The present invention relates to the use of ferric maltol compositions for the treatment or prevention of cancer and tumours, and in particular for the treatment or prevention of gastrointestinal cancers or gastrointestinal tumours, such as large bowel (colorectal), small bowel or upper gastrointestinal cancers.

BACKGROUND OF THE INVENTION

Oral iron supplementation is considered one of the main tools for preventing or treating iron deficiency and the associated anaemia in humans and other animals. Iron is a redox-active element and in changing between its reduced ($Fe^{2+}$, termed ferrous) and oxidised ($Fe^{3+}$, termed ferric) forms it induces free radicals which may then damage tissues. In this way, it is traditionally thought that simple iron salts can cause gastrointestinal side effects when delivered orally[1,2]. In light of which, different iron compounds have been developed. The use of iron chelation is one way to modify the iron environment such that it is both soluble in the gut lumen, and therefore absorbed, and protected from redox activity and thus acute side effects such as nausea, vomiting and gastrointestinal pain are reduced. Examples of chelated iron that may be used in this way are ferric citrate, ferric EDTA and ferric maltol.

However, it is established now that certain forms of chelated iron, namely ferric citrate and ferric EDTA, enhance intestinal cancer at least in animal models[3,4]. This is unsurprising because most supplemental iron is not absorbed. Even in patients with iron deficiency anaemia, less than 50% of iron from an oral iron supplement will be absorbed. The remainder will traverse the bowel and be excreted in faeces. Since these chelators aim to render the iron soluble in the gastrointestinal lumen for absorption in the proximal and mid small bowel, they should also be expected to render at least some of the iron available for cell uptake, in the distal gut. The distal gut, specifically the large bowel, is the major site of intestinal tumorigenesis in humans and it is well established that cells with a malignant potential or phenotype require iron for growth and survival. Thus supplemental iron that remains bioavailable to cells in the colon has the potential to promote tumourigenesis[3,4]. Similarly, for malignant or pre-malignant cells that, more rarely, are found elsewhere in the gut but away from the large bowel, bioavailable iron is anticipated to enhance their tumorigenic potential.

SUMMARY OF THE INVENTION

Broadly, the present invention is based on the inventors' insight that different forms of oral iron supplements cause different effects on cancer cells of the gastrointestinal tract, specifically that ferric maltol is detrimental (unfriendly) to gastrointestinal cancer cells as opposed to other forms of supplemental iron which are beneficial (friendly) to gastrointestinal cancer cells. Oral iron supplementation in humans is typically estimated to lead to luminal concentrations of 50 to 200 micromolar iron (see for example Mergler et al., *Journal of Pharmacy and Nutrition Sciences*, 2012, 2, 27-34). The present invention is based on the finding that in a series of three different gut epithelial cancer cell lines, and under two different conditions of cell culture, ferric citrate, ferric EDTA and the commonly used iron supplement, ferrous sulphate, all promote proliferation of the cells at concentrations that are predicted to occur in the gut lumen with iron supplementation. In contrast, and surprisingly, at typical iron supplemental levels, the present invention shows that ferric maltol inhibits cancer cell proliferation in all of the cancer cell lines tested. This means that in addition to its use in supplementation, ferric maltol compositions may be used in the treatment or prevention of cancer or tumours, in particular cancers or tumours of the gastrointestinal tract such as colorectal (herein including all cancers or tumours affecting the large bowel, for example those of the anus, rectum, colon and caecum), small bowel (herein including cancers or tumours affecting the duodenum, jejenum or ileum) or upper gastrointestinal region (herein including cancers or tumours affecting the stomach, oesophagus or mouth). The term gastrointestinal cancers or tumours includes gastrointestinal tissues or areas of gastrointestinal tissue that can be adjudged by those in the art, such as specialist doctors and surgeons as: pre-cancerous, at risk of cancer, cancerous or tumour-bearing. This includes the various sphincters of the gut and interaction with the pancreatic/hepato-biliary system and includes cancers or tumours of a primary or non-primary nature but that have some location in the gastrointestinal region.

The results described herein are particularly surprising as uncomplexed maltol, i.e. without being bound to iron, shows moderate inhibition of the cancer cell proliferation and, in this respect, is very similar to the effects of EDTA when it is not bound to iron. However, of particular surprise is that whilst the EDTA effect is actually attenuated by its binding to iron, the maltol effect is amplified. In other words, these two chelators that are used in iron supplementation display polar effects when bound to iron in terms of their cancer cell inhibition properties.

Not only, therefore, do the above data inform upon the choice of oral iron supplement for patients at risk of, or with, a gastrointestinal (GI) cancer, they provide a means to treat or prevent GI tumours whilst, beneficially, still delivering iron. In this latter case the iron could be in an oral preparation designed for targeted delivery in the gut, such as direct to the small bowel using enteric coating or to the large bowel using coatings that are time release or respond to pH or bacteria etc. The amphipathic nature of ferric maltol supports its absorption anywhere in the bowel.

Accordingly, in a first aspect, the present invention provides a ferric maltol composition for use in a method for the treatment and/or prevention of gastrointestinal cancer or gastrointestinal tumour in a subject.

In a further aspect, the present invention provides the use of a ferric maltol composition in the manufacture of a medicament for use in treating and/or preventing gastrointestinal cancer or gastrointestinal tumour in a subject.

In a further aspect, the present invention provides a method of treating and/or preventing a gastrointestinal cancer or a gastrointestinal tumour in a subject, the method comprising administering to the subject a therapeutically or prophylactically effective amount of a ferric maltol composition as defined herein.

In a further aspect, the present invention may be used for the treatment of (risk of) iron deficiency (anaemia) in patients at risk of developing a gastrointestinal cancer or a gastrointestinal tumour.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Ferric Maltol Compositions and their Uses

Figure 1:
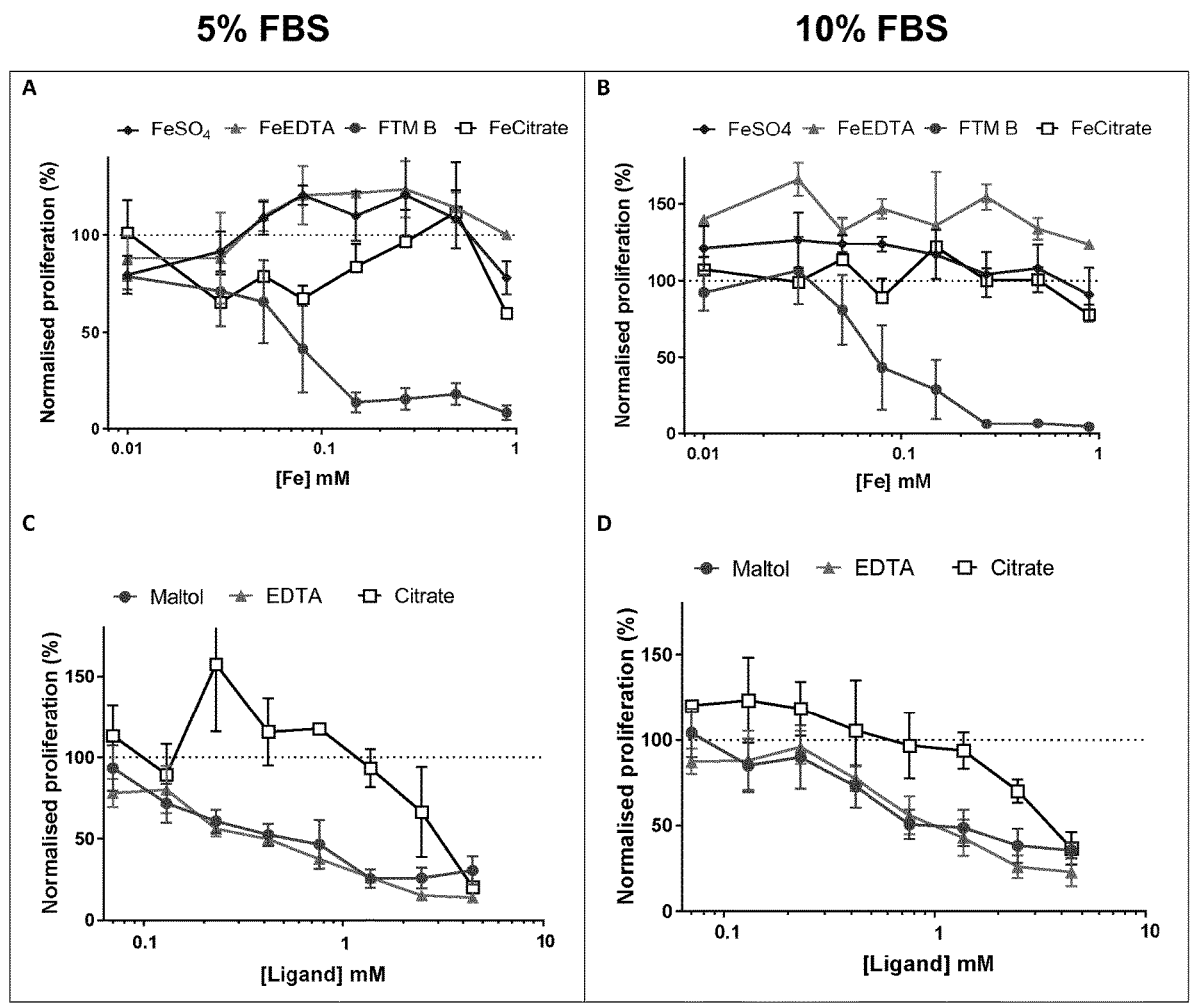
FIG. 1. Inhibition of cell proliferation in the Caco2 human epithelial colorectal adenocarcinoma cell line with different iron compounds as assessed by real time live cell imaging (Incucyte™). Cells were treated for 72 h with the indicated iron compounds in complete growth media containing 5% FBS (A) or 10% FBS (B), the corresponding 'ligand-only' controls are shown in panels C and D. Normalised cell proliferation corresponds to the area under the proliferation curve for cells grown in media supplemented with each compound divided by the area under the curve for cells grown in media alone (i.e. without any of the supplemented compounds). Data are presented as mean with SEM (n=3 independent experiments with 3 replicates for each experiment).

Ferric maltol is a form of chelated iron that generally has three maltol (3-hydroxy-2-methyl-4-pyrone) molecules surrounding a central iron atom (ferric trimaltol or also written ferric tri-maltol). Thus, ferric trimaltol is a chemical complex formed between ferric iron ($Fe^{3+}$) and the hydroxypyrone, maltol (IUPAC name: 3-Hydroxy-2-methyl-4H-pyran-4-one), in a molar ratio of ferric iron to maltol of 3:1. It may be specifically synthesised as the 3:1 molar complex or it may be created in solution by mixing, at a molar ratio, three or more maltols to one iron. However, it is well known that when dissolved in aqueous environments, including the gut, there may be other concentration-dependent and pH-dependent equilibrium species formed, including oligomers such as dimers, or iron species with one or two maltol molecules. Ferric trimaltol in solid or powder form may also exist as oligomers including dimers and not every iron is necessarily co-ordinated to three maltol molecules, but the term ferric tri-maltol is conventionally used in the art.

Accordingly, in the present application, references to "ferric maltol" are intended to include ferric iron species complexed with one, two or three maltol species, as well as oligomeric species such dimers and other species that may exist in equilibrium with them, and to mixtures of any of these species, even though the behaviour of the complex is believed to be dominated by its trimaltol form at supplemental levels[5,6]. The complex is amphipathic and thus is able to dissolve in aqueous environments such as the gut lumen, but then also cross into the lipid rich layer of cells. As such, it is expected to have good bioavailability and this, for example, has been shown in a number of studies including in patients with inflammatory bowel disease where ferric maltol effectively delivers iron to correct iron deficiency anaemia[7]. Moreover, given its amphipathic properties, ferric maltol would be expected to be absorbed at least to some extent anywhere in the intestinal tract.

Maltol strongly chelates iron. For all of these reasons the resulting ferric maltol complex (especially ferric trimaltol) provides a well absorbed form of iron, in contrast to many other ferric iron therapies. The structure of ferric trimaltol is shown in WO 2015/101971 (Iron Therapeutics Holdings AG). Ferric trimaltol is also known as "ST10" and is generally administered as a 30 mg dose, where 30 mg refers to the amount of iron in the dose but could equally be administered in a lower dose such as 20 mg or a higher dose such as 60 mg. The amount of ST10 equivalent to 30 mg of elemental iron ($Fe^{3+}$) is 231.5 mg. Ferric trimaltol is advanced in clinical trials for the treatment or prevention of iron deficiency anaemia in particular in patients with inflammatory bowel disease (IBD) or in patients with intolerance of other iron supplements. Methods for producing ferric trimaltol are described, inter alia, in WO 03/097627 and WO 2012/101442.

In the present invention, the subject may be human or a non-human animal, for example including veterinary uses for the treatment of animals such as dogs, cats and horses.

The ferric maltol compositions used in accordance with the present invention may be formulated for administration to an individual and contain in addition to ferric maltol, a pharmaceutically acceptable excipient, carrier, buffer, stabiliser or other materials well known to those skilled in the art. Such materials should be non-toxic and should not interfere with the efficacy of the ferric maltol.

The precise nature of the carrier or other component may be related to the manner or route of administration of the composition. These compositions may be delivered by a range of delivery routes including, but not limited to: gastrointestinal delivery, including orally and per rectum or by implantation at specific sites, including prosthetics that may be used for this purpose or mainly for another purpose but have this benefit.

Pharmaceutical compositions made according to the present invention are generally for oral administration and may be in a tablet, capsule, powder, gel or liquid form. A tablet may include a solid carrier such as gelatin and contain excipients. Capsules may have specialised properties such as an enteric coating.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The ferric maltol compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability and/or anti-cancer potential). The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated. Generally, the ferric maltol compositions are administered orally to a subject once, twice, three times or four times a day. Typically, the dosages administered comprise less than 200 mg/dose of iron, preferably less than 100 mg/dose, more preferably less than 70 mg/dose. Preferred examples of doses of the ferric maltol composition comprise 3-201 mg/dose of iron as ferric maltol, preferably 5-100 mg/dose, more preferably 10-70 mg/dose, more preferably 18-65 mg/dose and most preferably 18-65 mg/dose.

The ferric maltol compositions of the present invention may be used in the treatment or prevention of cancer or tumours, in particular cancers or tumours of the gastrointestinal tract such as colorectal (herein meaning all cancers or tumours affecting the large bowel including those of the anus, rectum, colon and caecum), small bowel (herein meaning cancers or tumours affecting the duodenum, jejenum or ileum) or upper gastrointestinal region (herein meaning cancers or tumours affecting the stomach, oesophagus or mouth). The term "gastrointestinal cancers or tumours" includes gastrointestinal tissues or areas of gastrointestinal tissue that can be adjudged by those in the art, such as specialist doctors and surgeons as: pre-cancerous, at risk of cancer, cancerous or tumour-bearing. This includes the various sphincters of the gut and aspects of the pancreatic/hepato-biliary system that are considered part of the gastro-intestinal system by those in the art. Generally, the ferric maltol compositions are orally administered, although the compositions may be formulated so that the ferric maltol is targeted for delivery in the gut, for example to direct the composition to the small bowel using an enteric coating or to the large bowel using coatings that are time release or respond to pH or bacteria etc. The amphipathic nature of ferric maltol supports its absorption anywhere in the bowel. The ferric maltol compositions of the present invention may be used in the treatment of primary or secondary cancer or tumours, and to access layers such as the epithelial, mucosal or sub-mucosal regions of the gastrointestinal tract or of the gut muscle layers or lymph nodes. The cancer or tumour may affect for example regular gut tissue and cells including the layers noted above, lymphoid tissue and cells, endocrine cells, stem cells, stromal cells or lymph nodes associated with the gut.

Generally, enteric coatings are a polymer barrier applied on oral medication such as tablets or capsule that slow or prevent its dissolution or disintegration in the gastric environment. This helps by protecting the active component of formulations (here ferric maltol compositions) from the potentially degradative acidity of the stomach, or to release the active component after the stomach. The use of enteric or other such coatings enables drug targeting to be achieved, for example allowing delivery of the active component to different locations in the gastrointestinal tract. As well as the use of enteric coatings, enteric delivery forms can be used to achieve the same effect by adding enteric polymeric systems to the matrix of the dosage form, for example in the form of mini-tablets, pellets and granules. Most enteric coatings work by presenting a surface that is stable at the highly acidic pH found in the stomach, but breaks down rapidly at a less acidic (relatively more basic) pH. For example, they will not dissolve in the gastric acids of the stomach (pH ~3), but they will in the alkaline (pH 4-9) environment present in the small intestine, small bowel or large bowel. The time required for an enteric-coated dosage form to reach the intestine mostly depends on the presence and type of food in the stomach and the choice of coating. When the active component reaches the less acidic, neutral or alkaline environment of the intestine, its active ingredients can then dissolve and become available at the intended site of action in the gastrointestinal tract. Alternatively or additionally, coatings may be employed that have a time delay before dissolution of the capsule or tablet to release its contents in the intestinal tract, or these coatings may respond to and dissolve in the presence of site-specific components of the intestinal tract such as the presence of bacteria, thus enabling delivery to the more distal intestine and especially the large bowel that includes the rectum, colon and caecum. Materials used for all these different types of coating for intestinal site specific release of the contents of an orally delivered formulation are well known in the art and include but are not limited to fatty acids, waxes, shellac, plastics, and plant fibres. Other conventional materials used are solutions of film resins.

Time release compositions generally involve formulation of the active components (here, ferric maltol compositions) by embedding it in a matrix of insoluble substance(s), such as but not limited to acrylic or chitin such that the dissolving active component must find its way out through the holes in the matrix. In some time release formulations, the active component dissolves into the matrix, and the matrix physically swells to form a gel, allowing the active component to exit through the gel's outer surface. A similar effect may be achieved using micro-encapsulation, which can enable more complex dissolution profiles to be achieved, for example by an active component ingredient around an inert core, and layering it with insoluble substances to form a microsphere one can often obtain more consistent and replicable dissolution rates in a convenient format. As well as the more conventional synthetic methods that are well known in the art, three dimensional printing is one recognised way of achieving such complex delivery systems.

In some embodiments, the use of the ferric maltol compositions of the present invention may be combined or used in conjunction with other therapies given to the subject, for example the ferric maltol may be administered in combination with surgery, radiation therapy, chemotherapy, immunotherapy and/or other targeted therapies. As ferric maltol compositions are comparatively well tolerated, this means that they are likely to combine well with other cancer therapies, many of which have side effects that limit their use, either alone or in combination.

As an alternative to oral delivery of the ferric maltol compositions, it may be desirable to have the ferric maltol composition delivered non-orally, for example per rectum, venously, percutaneously or parenterally. In one embodiment, the ferric maltol composition may be delivered to a desired site in the gastrointestinal tract via a tube or endoscope.

In some embodiments, the ferric maltol compositions may be used for the prevention of cancer in the subject. Optionally, this preventative treatment may be also be used to provide the treatment of subjects who are iron deficient or at risk of iron deficiency or else are in need of iron supplementation. By way of examples, the ferric maltol compositions may be used to deliver iron to an individual for use in the prophylaxis or treatment of iron deficiency or iron deficiency anaemia which may be suspected, or diagnosed through standard haematological and clinical chemistry techniques. Iron deficiency and iron deficiency anaemia may occur in isolation, for example due to inadequate nutrition or due to excessive iron losses, or they may be associated with stresses such as pregnancy or lactation, or they may be associated with diseases such as inflammatory disorders, cancers and renal insufficiency. In addition, there is evidence that the reduced erythropoiesis associated with anaemia of chronic disease may be improved or corrected by the effective delivery of systemic iron and that co-delivery of iron with erythropoietin or its analogues may be especially effective in overcoming reduced erthropoietic activity. Anaemia of chronic disease may be associated with conditions such as renal insufficiency, cancer and inflammatory disorders. As noted above, iron deficiency may also commonly occur in these disorders so it follows that treatment through iron supplementation may address iron deficiency alone and/or ameliorate anaemia of chronic disease. Of particular benefit will be the administration of ferric trimaltol to patients with or at risk of cancer as they will have or be at risk of anaemia. It will be recognised by those skilled in the art that the above examples of the medical uses of iron supplements are by no means limiting.

EXAMPLES

Materials and Methods
Iron Materials

Ferrous sulphate heptahydrate ($FeSO_4$) and ferric EDTA sodium salt (FeEDTA) were purchased from Sigma Aldrich. Ferrous sulphate was dissolved in acidified ultrapure water to produce the 40 mM [Fe] stock solution. Ferric EDTA was dissolved in ultrapure water to produce the 8 mM [Fe] stock solution. A stock solution of ferric citrate (FeCitrate) 8 mM [Fe] was produced by adding citric acid to ferric chloride on a 1:1 molar ratio. Ferric trimaltol (FTMB) was produced from iron hydroxides and maltol, and the stock solution of circa 8 mM [Fe] was produced by dissolving it in ultrapure water. All stock solutions were filter sterilised (0.2 µm).

Cell Culture

Three different epithelial cancer cell lines were used: colorectal adenocarcinoma [Caco2 (ATCC) and HT29 (ECAAC)] and duodenum adenocarcinoma [Hutu 80 (ATCC)]. The cells were grown in an incubator at 37° C. and an atmosphere of 5% $CO_2$ and 95% air at a relative humidity of approximately 95%. The cancer cells were grown in Gibco® MEM supplemented with 5 or 10% foetal bovine serum (FBS) as stated, 1% penicillin/streptomycin (10.000 Units/ml Penicillin, 10.000 µg/ml Streptomycin) and 1% fungizone (Amphotericin B, 250 µg/ml).

Proliferation Assay

Working solutions of 2 mM [Fe] for each iron compound were prepared fresh on the day of the experiment by diluting the stock solutions of the different iron materials in complete cell growth medium and these 2 mM solutions were used in the serial dilutions to achieve the 8 different concentrations for the proliferation assay (0.89, 0.49, 0.27, 0.15, 0.08, 0.05, 0.026, 0.015) in 96-well ImageLock cell culture plates. A control condition containing only complete growth medium without any iron compound added was also tested. The cells were seeded at a density of 10,000-20,000 cells/well. The plates were incubated in a Live Content Imaging Incubator (Incucyte ZOOM, Essen BioScience Ltd., UK) and images and confluence data were acquired every 3 hours for 72 hours post-seeding. Within each experiment each iron concentration was tested in triplicate wells.

Data Analysis

The plot of confluence (%) vs time (h) was obtained for each iron compound and concentration. The area under the curve (AUC) was calculated and plotted against the concentration for each test compound or the control. The AUC for each iron compound was normalised against that of the control (i.e. complete growth medium alone).

Results

Figure 2:
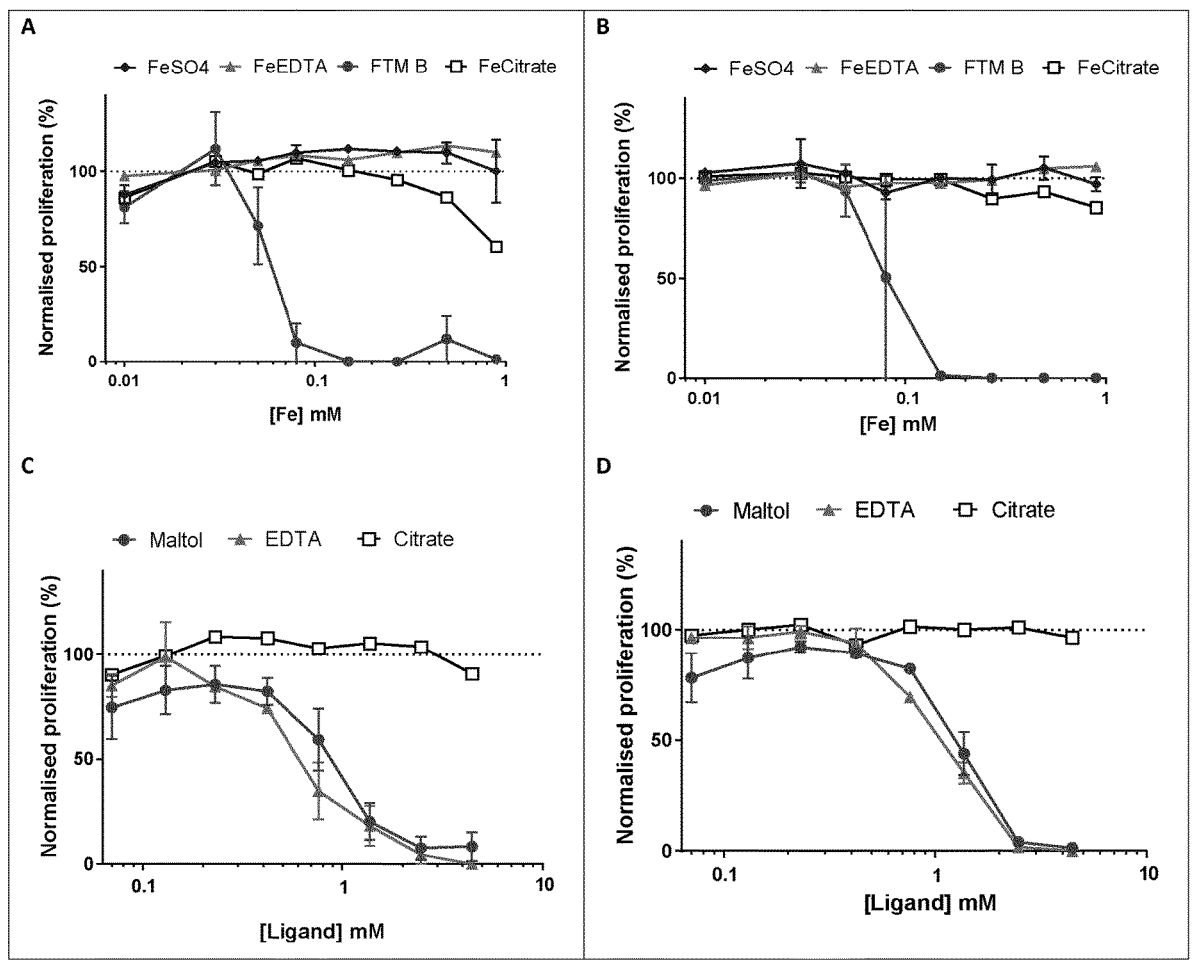
FIG. 2: Inhibition of cell proliferation in the Hutu 80 human epithelial duodenum adenocarcinoma cell line with different iron compounds as assessed by real time live cell imaging (Incucyte™) Cells were treated for 72 h with the indicated iron compounds in complete growth media containing 5% FBS (A) or 10% FBS (B), the corresponding 'ligand-only' controls are shown in panels C and D. Normalised cell proliferation corresponds to the area under the proliferation curve for cells grown in media supplemented with each compound divided by the area under the curve for cells grown in media alone (i.e. without any of the supplemented compounds). Data are presented as mean with SEM (n=2 independent experiments with 3 replicates for each experiment).
Figure 3:
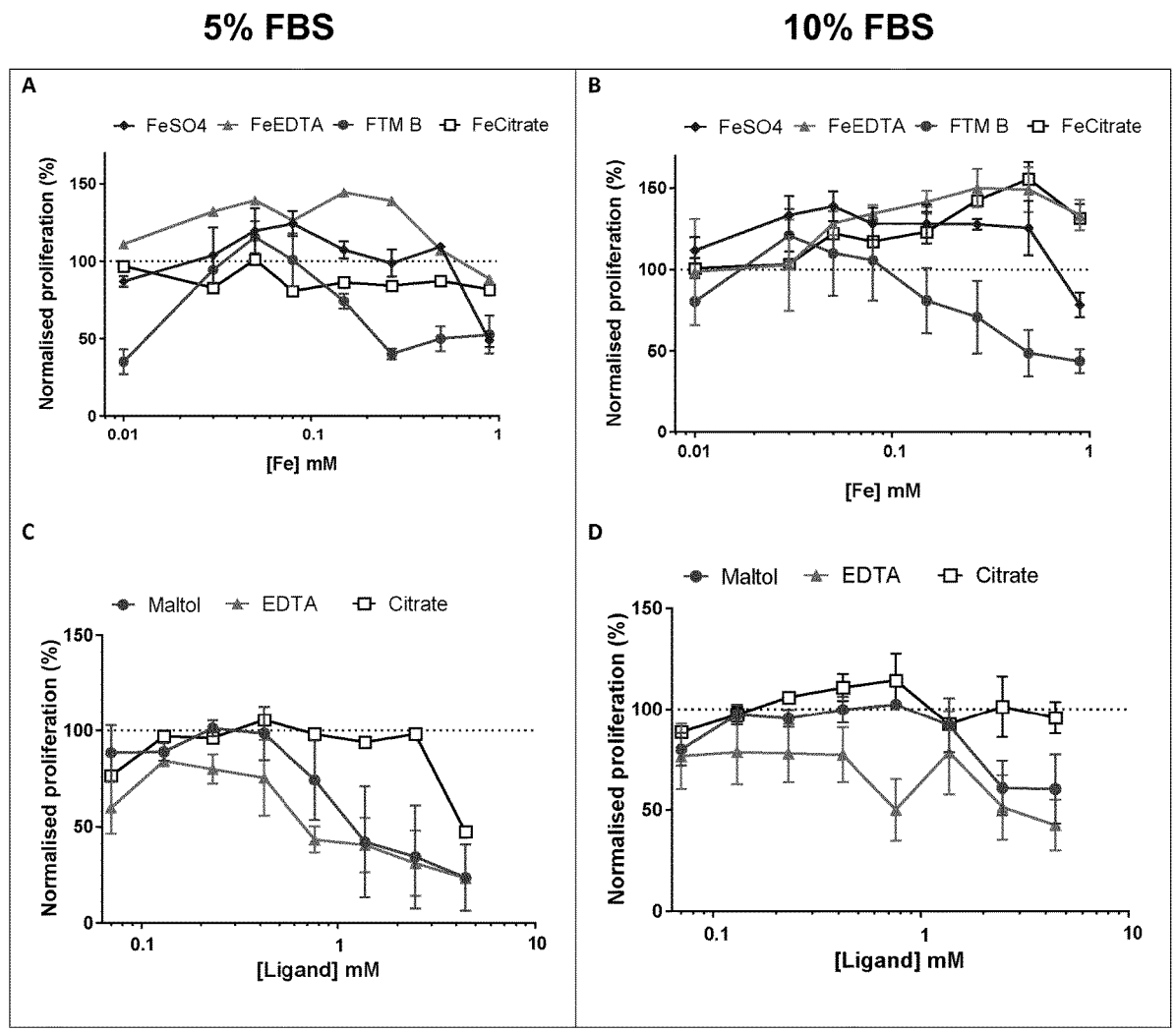
FIG. 3: Inhibition of cell proliferation in the HT29 human epithelial colorectal adenocarcinoma cell line with the different iron compounds as assessed by real time live cell imaging (Incucyte™). Conditions were as above in the legend to FIG. 2.

In this series of three different gut epithelial cancer cell lines, and under two different conditions of cell culture (5 or 10% FBS concentration) ferric citrate, ferric EDTA and the commonly used iron supplement, ferrous sulphate, all promoted proliferation of the cells at concentrations that are predicted to occur in the gut lumen with iron supplementation (FIG. 1-3). This is consistent with prior in vivo data showing that at least some of these forms of iron can promote intestinal tumourigenesis when delivered orally. In contrast, and surprisingly, at typical iron supplemental levels, ferric trimaltol actually inhibited cancer cell proliferation in all cases (FIGS. 1-3).

Interestingly the maltol molecule itself, without being bound to iron, showed moderate inhibition of the cancer cell proliferation and, in this respect, was very similar to the effects of EDTA that was not bound to iron (FIGS. 1-3). However, of particular surprise is that whilst the EDTA effect was actually attenuated by its binding to iron, the maltol effect was amplified. In other words, the data shows that these two chelators that are used in iron supplementation display polar effects when bound to iron in terms of their cancer cell inhibition properties.

When the real time-recorded cell images were reviewed it was clear that Caco2 and HT29 cells were poorly proliferating with 50 micromolar iron, as ferric trimaltol, and were non-proliferative with 80 micromolar iron as ferric trimaltol. For the duodenal adenocarcinoma (Hutu 80) cells these figures were 150 and 400 micromolar respectively. Thus, cancer cell proliferation can be arrested, or at least inhibited, using ferric trimaltol at levels that might be found in the gut lumen upon normal iron supplementation. Even a level of 400 micromolar would be achievable with higher supplemental levels and/or specific targeting of ferric maltol formulations in the gut as described above. This would be beneficial to human and other animal subjects.

REFERENCES

All publications, patent and patent applications cited herein or filed with this application, including references filed as part of an Information Disclosure Statement are incorporated by reference in their entirety.
1. Ferrous sulfate supplementation causes significant gastrointestinal side-effects in adults: a systematic review and meta-analysis. Tolkien Z, Stecher L, Mander A P, Pereira D I, Powell J J. PLoS One. 2015 Feb. 20; 10(2):e0117383. doi: 10.1371/journal.pone.0117383. eCollection 2015. Review.
2. A rapid, simple questionnaire to assess gastrointestinal symptoms after oral ferrous sulphatesupplementation. Pereira D I, Couto Irving S S, Lomer M C, Powell J J. BMC Gastroenterol. 2014 Jun. 4; 14:103. doi: 10.1186/1471-230X-14-103
3. Luminal iron levels govern intestinal tumorigenesis after Apc loss in vivo. Radulescu S, Brookes M J, Salgueiro P, Ridgway R A, McGhee E, Anderson K, Ford S J, Stones D H, Iqbal T H, Tselepis C, Sansom O J. Cell Rep. 2012 Aug. 30; 2(2):270-82. doi: 10.1016/j.celrep.2012.07.003. Epub 2012 Aug. 9
4. Systemic iron supplementation replenishes iron stores without enhancing colon carcinogenesis in murine models of ulcerative colitis: comparison with iron-enriched diet. Seril D N, Liao J, Yang C S, Yang G Y. Dig Dis Sci. 2005 April; 50(4):696-707
5. Bruggraber S F A, Hider R C and Powell J J. Does ferric-maltol speciation model defined by electrospray ionisation mass spectrometry fit the spectrophotometry/potentiometry data? In Pele L, Powell J J, Kinrade S, Jugdaohsingh R, Collery P, Maymard I, and Badawi A. (Eds.). Metal Ions in Biology and Medicine, vol 11. John Libbey Eurotext, Paris 2011, pp 158-163.
6. Bruggraber S F A, Langley G and Powell J J. Direct identification of iron (III) complexes In Pele L, Powell J J, Kinrade S, Jugdaohsingh R, Collery P, Maymard I, and Badawi A. (Eds.). Metal Ions in Biology and Medicine, vol 11. John Libbey Eurotext, Paris 2011, pp 152-157.
7. Ferric maltol is effective in correcting iron deficiency anemia in patients with inflammatory bowel disease: results from a phase-3 clinical trial program. Gasche C, Ahmad T, Tulassay Z, Baumgart D C, Bokemeyer B, Büning C, Howaldt S, Stallmach A; AEGIS Study Group. Inflamm Bowel Dis. 2015 March; 21(3):579-88.

The invention claimed is:

1. A method for the treatment of a gastrointestinal cancer or a gastrointestinal tumour in a subject in need thereof, comprising administering to said subject at least 80 mg iron equivalent per day of a ferric trimaltol composition.

2. The method according to claim 1, wherein the subject is human.

3. The method according to claim 1, wherein the subject is a non-human animal.

4. The method according to claim 1, wherein the ferric trimaltol is formulated for oral administration to the subject.

5. The method according to claim 1, wherein the gastrointestinal cancer is colorectal cancer or tumour, small bowel cancer or tumour, or upper gastrointestinal cancer or tumour.

6. The method according to claim 5, wherein the gastrointestinal cancer is a tumour of the colon and/or tumour of the rectum or tumour of the stomach.

7. The method according to claim 1, wherein the ferric trimaltol composition is formulated as a tablet or capsule.

8. The method according to claim 7, wherein the tablet or capsule comprises an enteric coating.

9. The method according to claim 1, wherein the ferric trimaltol composition is formulated as a tablet or capsule that comprises a time release coating and/or a pH-dependent release coating and/or a coating that responds to the presence of bacteria.

10. The method according to claim 1, wherein the composition is administered in combination with surgery, radiation therapy, chemotherapy, immunotherapy and/or natural product therapy.

11. The method according to claim 1, wherein the subject is anaemic or iron deficient or at risk of being anaemic or iron deficient or is in need of iron supplementation.

12. The method according to claim 1, wherein the composition comprises 3-201 mg/dose of iron as ferric trimaltol.

13. The method according to claim 1, wherein the composition is administered once, twice, thrice or four times a day.

14. The method according to claim 1, wherein the ferric trimaltol composition is delivered non-orally.

15. The method according to claim 1, wherein the ferric trimaltol composition is delivered per rectum.

16. The method according to claim 1, wherein the ferric trimaltol composition is delivered venously, percutaneously or parenterally.

17. The method according to claim 16, wherein the ferric trimaltol composition is delivered via a tube or endoscope.

18. The method according to claim 12, wherein the composition comprises 5-100 mg/dose.

19. The method according to claim 12, wherein the composition comprises 10-70 mg/dose.

20. The method according to claim 12, wherein the composition comprises 18-65 mg/dose.

21. The method according to claim 1, wherein the gastrointestinal cancer or a gastrointestinal tumour is a colorectal adenocarcinoma or a duodenum adenocarcinoma cancer or tumour.

* * * * *